United States Patent
Bermejo Osés et al.

(10) Patent No.: US 6,465,419 B1
(45) Date of Patent: Oct. 15, 2002

(54) ESTERS DERIVED FROM ALKANOLAMINES, DICARBOXYLIC ACIDS AND FATTY ALCOHOLS AND THE CATIONIC SURFACTANTS OBTAINABLE THEREFROM

(75) Inventors: María José Bermejo Osés; Josep Ferrer Vilaret; Marisa Tomás Mumbrú, all of Barcelona (ES)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/874,981

(22) Filed: Jun. 7, 2001

(51) Int. Cl.[7] .............................. C11D 3/32; C11D 1/62
(52) U.S. Cl. ...................... 510/515; 510/504; 564/296; 564/292
(58) Field of Search .................. 510/504, 515; 564/281, 288, 291, 292, 296

(56) References Cited

FOREIGN PATENT DOCUMENTS

| DE | 19715835 | * | 4/1997 |
|---|---|---|---|
| JP | 10-195767 | * | 7/1998 |
| WO | WO 96/35661 | * | 11/1996 |

* cited by examiner

Primary Examiner—John Hardee
(74) Attorney, Agent, or Firm—Oblon, Spivak, McClelland, Maier & Neustadt, P.C.

(57) ABSTRACT

Esters derived from alkanolamines, dicarboxylic acids and fatty alcohols and the cationic surfactants obtainable therefrom.

Novel alkanolamine esters based on the esterification reaction of alkanolarnines, optionally alkoxylated, dicarboxylic acids and fatty alcohols, optionally alkoxylated, as well as the cationic surfactants and esterquats obtainable therefrom, are described.

The cationic surfactants and esterquats thus obtained exhibit a high degree of efficacy in softening and conditioning natural and synthetic fibres such as textiles, paper and hair, and are therefore usable in treatments for softening and conditioning the said fibres.

Novel aqueous fabric-softening compositions which contain the cationic surfactants and esterquats mentioned, optionally in combination with other active softening substances, are also described.

15 Claims, No Drawings

ESTERS DERIVED FROM ALKANOLAMINES, DICARBOXYLIC ACIDS AND FATTY ALCOHOLS AND THE CATIONIC SURFACTANTS OBTAINABLE THEREFROM

DESCRIPTION

1. Technical Field

The present invention relates to novel esters derived from alkanolamines, dicarboxylic acids and fatty alcohols, and to the cationic surfactants obtainable therefrom, as well as to their use as softening agents for natural and synthetic fibres.

2. Prior Art

Cationic surfactants derived from amines have been used widely for some decades as softening and conditioning agents for natural and synthetic fibres of all types, and are used in fields such as the treatment of textile fibres and of paper and in hair hygiene products.

For ecological reasons, owing to their greater biodegradability, the use of cationic amine derivatives in which the hydrophobic hydrocarbon chains are interrupted by functional ester groups has been usual for several years, those used mostly being the quaternized derivatives of polyalkanolamine esters, generally known as esterquats, amongst which one of the types used most is esterquats derived from triethanolamine, owing to their lower cost.

It is also well known that the above-mentioned esterquats are prepared from alkanolamine esters, produced previously by an esterification reaction of the alkanolamine with fatty acids or functionalized reactive derivatives thereof, by their quaternization with alkylation agents such as alkyl halides or sulphates. There is an abundant bibliography on the subject, amongst which patents or patent applications FR-A-1593921, EP-A-239910, EP-A-295385, WO-A-9101295, DE-C-19539846 and WO-A-9849132, amongst many others, may be mentioned.

However, it is well known that esterquats are less effective softeners than their homologues which do not contain ester groups, and this has led to various technical developments directed towards improving the softening efficacy of these esterquats.

Thus, patent U.S. Pat. No. 5,593,614 describes the improvement of the softening effect of esterquats by mixing them with non-ionic surfactants, patent U.S. Pat. No. 5,501,806 proposes the mixing of esterquats with other cationic surfactants, and patent application EP-A-394133 describes the use of acrylic cationic polymers as additives for improving softness.

British patent GB-602048 describes oligomeric alkanolamine esters based on the esterification reaction of triethanolamine with dicarboxylic acids and fatty acids, as well as their quaternization with methyl chloride or dimethyl sulphate and their use as softening agents for natural and synthetic fibres, and patents U.S. Pat. No. 4,719,382 and U.S. Pat. No. 4,237,016 describe the use of the esterquats described in the above-mentioned British patent, amongst cationic polymers of many other types, as additives for improving the softening efficacy of cationic surfactants which do not contain ester groups. Moreover, patent application WO-A-9812293 describes the use of the same oligomeric esterquats as additives for incorporation in the aqueous phase of softening compositions which contain esterquats, with the object of improving their softening efficacy.

German patent DE-C-19539846 describes the synthesis of esterquats derived from dicarboxylic acids, fatty acids and triethanolamine and their use as hair conditioners, and patent DE-C-19715835 describes esterquats based on the reaction of methyl diethanolamine and mixtures of fatty acids and dicarboxylic acids, with subsequent ethoxylation and/or quaternization.

Patent WO-A-9849132 describes the synthesis of esterquats derived from dicarboxylic acid/fatty acid/triethanolamine, within a specific selected range of proportions, and their use in fabric-softening compositions.

Lastly, patent DE-C-19519876 describes esterquats based on the reaction of a trialkanolamine with mixtures of fatty acids, dicarboxylic acids, and sorbitol and the subsequent quaternization and/or ethoxylation of the esters produced.

However, as far as the authors of the present invention know, the prior art always relates to alkanolamine esters and to their corresponding esterquats in which the hydrophobic chains result directly and mainly from the esterification of fatty acids, so that no descriptions have been found of alkanolamine esters and their corresponding esterquats in which the hydrophobic chains result mainly from fatty alcohols combined with the cationic portion of the molecule by means of a dicarboxylic-acid bridge and which, moreover, have a high degree of biodegradability and a greater softening efficacy than that of conventional esterquats.

SUMMARY OF THE INVENTION

The subject of the present invention is novel esters derived from alkanolamines, dicarboxylic acids and fatty alcohols, and the cationic surfactants obtainable therefrom.

Also included within the subject of the present invention is the use of the cationic surfactants based on the said esters derived from alkanolamines, dicarboxylic acids and fatty alcohols, particularly the esterquats obtainable therefrom, as conditioning and softening agents for natural and synthetic fibres.

Also included within the subject of the present invention are aqueous softening compositions for textile fibres containing, either as the active ingredient or as an additive for improving softening efficacy, cationic surfactants based on the said esters derived from alkanolamines, dicarboxylic acids and fatty alcohols, particularly the esterquats obtainable therefrom.

DESCRIPTION OF THE INVENTION

The alkanolamine esters of the invention are obtained by the esterification reaction of an alkanolamine of general formula (I)

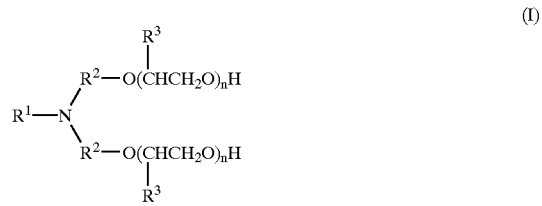

with a dicarboxylic acid or with a reactive derivative thereof, of general formula (II)

$$HOOC-R^4-COOH \qquad (II)$$

and with a fatty alcohol, optionally alkoxylated, of general formula (III)

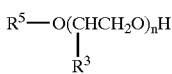

in which formulae $R^1$ is hydrogen, a $C_1$–$C_6$ alkyl group, or the residue

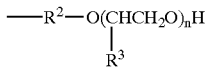

$R^2$ is a $C_1$–$C_6$ alkylene group, $R^3$ is hydrogen or methyl, n is 0 or a whole number between 1 and 20, $R^4$ is a $C_1$–$C_{36}$ alkylene group, optionally substituted or unsaturated, or an arylene group, and $R^5$ is a linear or branched $C_2$–$C_{22}$ alkyl or alkenyl group.

Optionally, a fatty acid of general formula (IV) may also be incorporated in the reaction mixture $$R^6\text{—COOH} \qquad (IV)$$

in which $R^6$ is a linear or branched $C_6$–$C_{23}$ alkyl or alkenyl group, an alkyl ester, a glyceride of the fatty acid, and/or a polyol, optionally alkoxylated.

The invention provides a cationic surfactant obtainable by the formation of the addition salt of the alkanolamine ester as above defined with mineral or organic acids.

The invention provides an esterquat obtainable by quaternization of the alkanolamine ester as above defined by the reaction with alkylation agents.

The invention besides provides a method of treating softening and/or conditioning treatment of natural or synthetic fiber, textile, paper fiber or hair fiber with the esterquats as above defined.

The invention further provides an aqueous fabric-softening composition which comprises:
  (a) a surfactant or an esterquat thereof as above shown,
  (b) one or a plurality of cationic surfactants active as fabric softeners,
  (c) one or a plurality of non-ionic fabric-conditioning surfactants, in which the total amount of components (a), (b) and (c) is between 2% and 60% by weight in a manner such that, with respect to the total amount of the said components (a), (b) and (c),
    (i) the proportion by weight of component (a) is between 2% and 99%,
    (ii) the proportion by weight of component (b) is between 0% and 98%,
    (iii) the proportion by weight of component (c) is between 0% and 40%, and
    (iv) the proportion by weight of the total amount of (b) and (c) is between 1% and 98%.

It is preferable that that the total amount of components (a), (b) and (c) is between 3% and 40% by weight,
  (i) the proportion by weight of component (a) is between 3% and 80%,
  (ii) the proportion by weight of component (b) is between 0% and 97%,
  (iii) the proportion by weight of component (c) is between 0% and 30%, and
  (iv) the proportion by weight of the total amount of (b) and (c) is between 20% and 97%.

DETAILED DESCRIPTION OF INVENTION

The following may be mentioned as examples of alkanolamines which may be used: triethanolamine, N-methyl diethanolamine, N-methyl diisopropanolamine and triisopropanolamine, optionally alkoxylated with ethylene oxide or propylene oxide, or mixtures thereof, the non-alkoxylated alkanolamines, particularly triethanolamine, being preferred.

As examples of dicarboxylic acids, without intending to provide an exhaustive list, it is possible to mention succinic, malic, glutaric, adipic, sebacic, pimelic, suberic, maleic and terephthalic acids and also those known as dimers of fatty acids or dimeric fatty acids, which are produced by thermal oligomerization of unsaturated fatty acids, such as those marketed by Unichema International under the name PRIPOL[7], for example, PRIPOL[7] 1009, or mixtures of the said acids. Adipic acid is preferred.

The fatty alcohols of formula (III), optionally alkoxylated with ethylene oxide or propylene oxide, may be hydrogenated or non hydrogenated fatty alcohols obtained from fats and oils of natural origin, for example, from tallow, palm, olive, coconut, sunflower, soya, grape marc or rape etc., non-alkoxylated alcohols which contain mainly between 16 and 18 carbon atoms being preferred.

Examples of fatty acids which may optionally be included in the esterification reaction are those obtained from vegetable and animal oils and fats such as those obtained from coconut, tallow, palm, sunflower, soya, olein, oil greaves, etc., optionally wholly or partially hydrogenated, as well as purified or synthetic fatty acids such as lauric, stearic, palmitic, oleic, linoleic, and 2-ethylhexanoic acids, etc.

The polyols which may also optionally be included in the esterification reaction may be, for example, glycerol, pentaerythritol, sucrose, glucose, sorbitol, or glycols such as ethylene glycol, propylene glycol, diethylene glycol, dipropylene glycol, etc.

Advantageously, for the purposes of the present invention:
  X the molar ratio of the dicarboxylic acid to the alkanolamine is between 0.2 and 1.2, preferably between 0.3 and 0.9, most preferably between 0.4 and 0.8,
  X the molar ratio of the sum of the fatty alcohol and the fatty acid to the alkanolamine is between 0.2 and 2.0, and
  X the molar ratio of the fatty acid to the fatty alcohol is between 0 and 10, preferably between 0.1 and 5.0, most preferably between 0.5 and 1.0.
  X The esterification reaction is performed by methods known per se, such as that described in patent application WO-A-9849132 which is incorporated herein by reference.

The esterification reaction is preferably performed by condensation of the dicarboxylic acid, and optionally the fatty acid, with a mixture of the alkanolamine and the fatty alcohol, and optionally the polyol, at a temperature of between $120°C$ and $220°C$, for a period of from 2 to 10 hours, preferably at a reduced pressure of about 5 to 200 mbar and in the presence of some of the catalysts already known for the esterification of conventional esterquats, for example, hypophosphorous acid and paratoluene sulphonic acid, and also in the presence of some of the usual stabilizers and antioxidants such as tocopherols, BHT, BHA, citric acid, etc. The esterification reaction can also be performed by condensing the dicarboxylic acid with the triethanolamine in the first place and adding the fatty alcohol afterwards.

It will be clear to a person skilled in the art that the esterification reaction may alternatively also be performed by other conventional techniques starting with reactive derivatives of the dicarboxylic acids, for example, their esters, their anhydrides, or their acid chlorides.

The esters thus produced are useful for preparing cationic surfactants efficacious for use in the softening and conditioning treatment of natural and synthetic fibres such as textiles, paper and hair. The cationic surfactants may be the esterquats obtainable by their quaternization with alkylation agents, or addition salts of the alkanolamine esters of the invention with mineral or organic acids such as hydrochloric, sulphuric, phosphoric, citric, and lactic acids, etc. The esterquats are preferred as cationic fibre-softening surfactants.

The esterquats are produced from the alkanolamine esters of the invention by an additional quaternization reaction, also known per se, for example, as described in the above-mentioned patent application WO-A-9849132.

For example, the reaction mixture resulting from the esterification is reacted with alkylating products such as methyl chloride, methyl bromide, dimethyl sulphate, diethyl sulphate, dimethyl carbonate, etc., preferably in the presence of organic solvents which facilitate the handling thereof, such as isopropanol, ethanol, propylene glycol, ethylene glycol, dipropylene glycol, fatty alcohols, etc., and the pH is subsequently adjusted to between 1.5 and 7.0, preferably between 2 and 4.5 by the addition of an acid such as any of hydrochloric, sulphuric, phosphoric, citric acids, etc.

The cationic surfactants obtainable from the alkanolamine esters of the invention exhibit a high degree of fibre-softening efficacy and, moreover, owing to their degree of biodegradability, are very well tolerated from the ecological point of view. Moreover, even if the said surfactants are not used in a major or predominant proportion, they considerably improve the softening efficacy of compositions based on conventional esterquats and other cationic surfactants and, when used as fabric softeners, counteract the adverse effect of the presence of anionic surfactant residues in the textile fibres after washing and during the rinsing stage.

In summary, the cationic surfactants obtainable from the alkanolamine esters of the invention may be used as the basic substance of fabric softening or hair conditioning compositions and also as additives for softening compositions or detergents the main active component of which is another cationic surfactant, or a mixture therefrom. As well as improving the feel of the fabric, its use in fabric-softening formulations facilitates ironing and reduces the appearance of creases during washing and its use in hair-conditioning compositions or as an additive in shampoos improves combability and the appearance of the hair.

With some of the products defined in this patent, particularly those in which the fatty chains have unsaturated bonds, it is possible to produce softening formulations which are translucent or transparent without the need to use the solvents usually used for formulas of this type.

In particular, although not exclusively, the present invention includes aqueous fabric-softening compositions which contain:

(a) cationic surfactants or esterquats obtainable from the alkanolamine esters of the invention, (b) one or a plurality of cationic surfactants active as fabric softeners, (c) one or a plurality of non-ionic fabric-conditioning surfactants, in which the total amount of components (a), (b) and (c) is between 2% and 60% by weight, in a manner such that, with respect to the total amount of the said components (a), (b) and (c), (i) the proportion by weight of component (a) is between 2% and 100%, (ii) the proportion by weight of component (b) is between 0% and 98%, and (iii) the proportion by weight of component (c) is between 0% and 40%, the remaining constituents being water and other optional constituents selected from amongst those normally used in aqueous fabric-softening compositions.

Preferably, the aqueous fabric-softening compositions of the invention contain between 3% and 40% by weight of the total amount of components (a), (b) and (c) in a manner such that, with respect to the total amount of the said components (a), (b) and (c), (i) the proportion by weight of component (a) is between 3% and 80%, (ii) the proportion by weight of component (b) is between 0% and 97%, and (iii) the proportion by weight of component (c) is between 0% and 30%, the remaining constituents being water and other optional constituents selected from amongst those usually used in aqueous fabric-softening compositions.

The cationic surfactants which are active as fabric-softeners and which constitute component (b) of the softening compositions of the invention are well-known to persons skilled in the art.

Amongst these may be mentioned. the quaternary ammonium compounds the hydrophobic chains of which are not interrupted by an ester group, for example, those described in the patents U.S. Pat. No. 4,719,382 and U.S. Pat. No. 4,237,016, amongst which the best known is hydrogenated tallow dialkyldimethylammonium chloride also known as DTDMAC as marketed by KAO Corporation, S.A. under the mark QUARTAMIN[7] D86P.

However, the esterquats, descriptions of which, amongst many others, are to be found in the documents already cited in this description, which are incorporated herein by reference, are preferred and amongst those which may be mentioned as significant examples are the following:

X quatemized fatty-acid diesters with 1,2-dihydroxy-3-dimethylaminopropane, as described in U.S. Pat. No. 4,137,180 and European patent application EP-A-0585040, X quaternized fatty-acid diesters with N-methyl diethanolamine, such as those described in French patent application FR-A-1593921 and in European patent EP-B-0239910, for example, hydrogenated tallow diester quaternized with methyl chloride, marketed by KAO Corporation, S.A. under the mark KAOSOFT[7] PH, X salts of fatty-acid amidoesters with N-methyl-N-aminopropyl ethanolamine, for example, that marketed by KAO Corporation under the mark KAOSOFT[7] 1, X quaternized fatty-acid diesters with triethanolamine, such as those described in U.S. Pat. No. 3,915,867 and in a large number of subsequent patents, for example, diesters of partially hydrogenated tallow quaternized with dimethyl sulphate, which are marketed by KAO Corporation, S.A. under the marks TETRANYL[7] AT-7590 and TETRANYL[7] L1/90.

It should be pointed out that, when the term "diester" is referred to, it is intended to indicate that the diester is a major constituent of the mixture, although the product may still contain variable quantities of monoester compounds and, in the case of triethanolamine, of triester compounds.

Also included in this consideration of cationic surfactants of a softening nature are the oligomeric cationic surfactants described in patent application WO-A-9849132, for example, those marketed by KAO Corporation S.A. under the references TETRANYL[7] PH-2 and TETRANYL[7] PH-5. The fabric-conditioning non-ionic surfactants which constitute component (c) are also well known to persons skilled in the art and amongst them may be mentioned: fatty acids, fatty-acid esters, particularly linear or branched $C_8$–$C_{18}$ fatty-acid esters, alkoxylated or without alkoxylation, Guerbet alcohols alkoxylated or without alkoxylation, glycerol esters, sorbitan esters alkoxylated or without alkoxylation, for example, KAOPAN[7] marketed by KAO Corporation, S.A., sucrose esters, $C_{8-18}$ fatty alcohols, glycerol esters, optionally alkoxylated, for example, LEVENOL[7] marketed by KAO Corporation, S.A., and pentaerythritol esters, alkoxylated or without alkoxylation.

In so far as other optional components are referred to, although it should not be considered as an exhaustive description of all of the possibilities which, on the other hand, are well known to persons skilled in the art, the following may be mentioned:

a) Other products which improve the performance of the softening compositions, such as silicones, amine oxides, anionic surfactants such as lauryl ether sulphate or lauryl sulphate, amphoteric surfactants such as cocoamidopropyl betaine or the alkylbetaines, sulphosuccinates, polyglucosidate derivatives, etc.

b) Stabilizers such as salts of short-chain amines, quaternized or without quaternization, for example, of triethanolamine, N-methyl diethanolamine, etc., and also non-ionic surfactants such as ethoxylated fatty alcohols, ethoxylated fatty amines, ethoxylated alkylphenols, etc.

c) Products which improve viscosity control, for example, inorganic salts such as calcium chloride, magnesium chloride, calcium sulphate, sodium chloride, etc.; products which serve to reduce viscosity in concentrated compositions, such as glycol compounds, for example, ethylene glycol, dipropylene glycol, polyglycols, etc., and thickening agents for diluted compositions, for example, polymers derived from cellulose, guar gum, etc.

d) Components for adjusting the pH, which is preferably between 1.5 and 4.5, such as inorganic and/or organic acids of any type, for example, hydrochloric, sulphuric, phosphoric, and citric acids, etc.

e) Agents which improve "soil release", such as the known terephthalate-based polymers or copolymers.

f) Bactericidal preservatives such as formol, Kathon GC, Bronopol, etc.

g) Other products such as antioxidants, colouring substances, perfumes, germicides, fungicides, anticorrosive agents, anti-creasing agents, opacifiers, optical brightening agents, pearlizing agents, etc.

The softening compositions may be produced simply by mixing their constituents until they are dispersed or dissolved, with the use of methods well known to persons skilled in the art.

The following examples are given in order to provide a person skilled in the art with a sufficiently clear and complete explanation of the present invention but should not be considered as limiting of the essential aspects of its subject, as set out in the preceding portions of this description.

EXAMPLES

Examples 1 to 16

Preparation of the Alkanolamine Esters

The products of Table 1 were prepared with the use of the reagents and the quantities indicated in Table 1, in accordance with the following general esterification method:

The alkanolamine and the fatty alcohol and, where appropriate, the polyol, were mixed in a reaction flask equipped with a stirrer, a temperature probe and an inlet for an inert gas. The following are added as esterification catalysts: 50% by weight hypophosphorous acid in sufficient quantity to give a content of 1000 ppm relative to the total load or, alternatively, paratoluene sulphonic acid in sufficient quantity to give a content of 500 ppm relative to the total load. The mixture was heated to $100^F C$ in an inert atmosphere, the dicarboxylic acid and, where appropriate, the fatty acid, were added, the temperature was increased to $170^F C$, and this temperature was maintained whilst the esterification water was distilled until the acidity index of the mixture was below 5 mg KOH/g.

Where appropriate, the esterification product will be subjected to a conventional ethoxylation reaction with ethylene oxide.

TABLE 1

Reagents used in the esterification reaction

| Ex. | Amine | Dicarboxylic acid | Fatty alcohol or source therefor | Fatty acid or source therefor | Polyol |
|---|---|---|---|---|---|
| 1 | TEA (1 Mole) | Adipic (0.5 Moles) | Hydrogenated tallow (0.6 Moles) | — | — |
| 2 | TEA (1 Mole) | Adipic (0.7 Moles) | Hydrogenated tallow (1.2 Moles) | — | — |
| 3 | TEA (1 Mole) | Adipic (0.8 Moles) | Hydrogenated tallow (0.2 Moles) | Tallow (0.6 Moles) | — |
| 4 | TEA (1 Mole) | Adipic (0.5 Moles) | Hydrogenated tallow (0.2 Moles) | Tallow (0.5 Moles) | — |
| 5 | TEA (1 Mole) | Adipic (0.5 Moles) | Hydrogenated tallow (0.2 Moles) | Coconut (0.5 Moles) | — |
| 6 | TEA (1 Mole) | Adipic (0.7 Moles) | Hydrogenated tallow (0.1 Moles) | Oleic (0.9 Moles) | — |
| 7 | TEA (1 Mole) | Adipic (0.6 Moles) | Palm (0.8 Moles) | — | — |
| 8 | TEA (1 Mole) | Adipic (0.7 Moles) | Hydrogenated tallow (0.4 Moles) | — | — |

TABLE 1-continued

Reagents used in the esterification reaction

| Ex. | Amine | Dicarboxylic acid | Fatty alcohol or source therefor | Fatty acid or source therefor | Polyol |
|---|---|---|---|---|---|
| 9 | TEA (1 Mole) | Adipic (0.8 Moles) | Hydrogenated tallow (0.3 Moles) | 2-ethylhexanoic (0.8 Moles) | — |
| 10 | TEA (1 Mole) | PRIPOL⁷1009 (0.3 Moles) | Oleic (0.2 Moles) | Coconut (0.8 Moles) | — |
| 11 | TEA (1 Mole) | Adipic (0.5 Moles) | Hydrogenated tallow (0.1 Moles) | Tallow (0.6 Moles) | Glycerol (0.5 Moles) |
| 12 | TEA (1 Mole) | Adipic (0.6 Moles) | Hydrogenated tallow (0.2 Moles) | Tallow (0.8 Moles) | Sorbitol (0.25 Moles) |
| 13 | TEA (1 Mole) | Adipic (0.4 Moles) | Hydrogenated tallow (0.5 Moles) | Tallow (0.6 Moles) | — |
| 14 | TEA (1 Mole) | Adipic (0.6 Moles) | Hydrogenated tallow ethoxylated (5EO) (0.2 Moles) | Tallow (0.8 Moles) | — |
| 15 | TEA (1 Mole) | Adipic (0.8 Moles) | Hydrogenated tallow (0.1 Moles) | Tallow (0.5 Moles) | — |
| 16 | Product obtained in Example 4 subsequently ethoxylated with 3 moles of EO | | | | |

TEA: triethanolamine;
MDEA: methyl diethanolamine
PRIPOL⁷1009: dimer of fatty acid marketed by Unichema International The product obtained in the esterification, which constitutes the subject of the invention, is a very complex mixture of chemical compounds and is useful, in crude form as it is produced, for preparing the cationic surfactants and esterquats which are also subjects of the invention.

Example 17

Preparation of the Surfactant Addition Salts

The esterification product of Example 6 was loaded, together with the quantity of isopropyl alcohol sufficient to give a content of 15% thereof, relative to the total load, and the quantity of BHT necessary to give a content of 500 ppm relative to the total load, into a reaction flask equipped with a stirrer, a temperature probe, and a dropping funnel. The mixture was heated to $50°C$ and a 30% solution of hydrochloric acid was added to it, over a period of 1 hour, in the stoichiometric quantity necessary to salify all of the product, stirring being continued at a temperature of $50°-55°C$ for a further 1–2 hours.

The addition salts of other esterification products can be obtained in a similar manner either with hydrochloric acid or with other, different acids.

Examples 18 to 32

Preparation of the Esterquats

The esterquats of Table 2 were prepared with the use of the reagents indicated in Table 2, in accordance with the following general quaternization methods:

Quaternization with Methyl Chloride

The product resulting from the esterification step, together with sufficient quantity of isopropyl alcohol for the said alcohol to represent between approximately 8% and approximately 12% by weight relative to the crude quaternized product and, optionally, BHT in the quantity necessary to give a content of 500 ppm relative to the total load, were loaded into a reaction flask capable of working under pressure conditions and equipped with a stirrer, a dropping funnel, and a temperature probe. The mixture was heated to $85°-90°C$ and a quantity slightly greater than the stoichiometric quantity of methyl chloride was added, whilst the pressure was kept between 2 and 3 kg/cm². Upon completion of the addition of the methyl chloride, stirring of the reaction mixture was continued for 1–2 hours at $80°-85°C$.

Quaternization with Dimethyl Sulphate

The product resulting from the esterification step, together with sufficient quantity of isopropyl and/or ethyl alcohol to represent between approximately 8% and approximately 12% by weight relative to the finished product and, optionally, BHT in sufficient quantity to give a content of 500 ppm relative to the total load, were loaded into a 1-litre reaction flask equipped with a stirrer, a temperature probe, and a dropping funnel. The mixture was heated to $50°C$ and a quantity slightly less than the stoichiometric quantity of dimethyl sulphate was added slowly over 1–2 hours. Upon completion of the addition, stirring of the reaction mixture continued for a further 3–4 hours at $50°-55°C$.

TABLE 2

Reagents used in the quaternization reaction

| Example | Alkanolamine ester | Alkylation agent |
|---|---|---|
| 18 | that obtained in Example 1 | Dimethyl sulphate |
| 19 | that obtained in Example 2 | Methyl chloride |
| 20 | that obtained in Example 3 | Dimethyl sulphate |
| 21 | that obtained in Example 4 | Dimethyl sulphate |
| 22 | that obtained in Example 5 | Dimethyl sulphate |
| 23 | that obtained in Example 7 | Dimethyl sulphate |
| 24 | that obtained in Example 8 | Dimethyl sulphate |
| 25 | that obtained in Example 9 | Methyl chloride |
| 26 | that obtained in Example 10 | Dimethyl sulphate |
| 27 | that obtained in Example 11 | Dimethyl sulphate |
| 28 | that obtained in Example 12 | Dimethyl sulphate |
| 29 | that obtained in Example 13 | Dimethyl sulphate |
| 30 | that obtained in Example 14 | Dimethyl sulphate |
| 31 | that obtained in Example 15 | Dimethyl sulphate |
| 32 | that obtained in Example 16 | Dimethyl sulphate |

The esterquats thus obtained are also very complex mixtures of chemical compounds and are useful, in crude form as they are produced, for the preparation of compositions for softening and conditioning natural and synthetic fibres.

Example 33

Softness Tests on Fabrics

Softness tests of the cationic surfactants produced in accordance with the examples given above, as well as comparative tests performed with other, conventional cationic surfactants, were performed in conditions similar to those of actual use, by comparing the results obtained with doses corresponding, with two ratios of active softening substance in relation to the weight of textile fibre, that is: 0.1% and 0.2% by dry weight of solid active softening substance, relative to the weight of the fabric.

The tests were performed on cotton towels, by performing five washing operations and five softening operations, at the rinsing stage, one after each wash, with the use of water of $25^E$ HF (French degrees of hardness) in a MIELE[7] washing machine and with the use of the detergent sold on the Spanish market by the company Benckiser, under the trademark COLON[7].

The results were evaluated by calculation of the statistical mean of the values obtained on the basis of the quantification of the subjective opinion of twenty experienced panellists who used as references: a) a blank, consisting of a cotton towel which was not treated with softener after washing, to which the value 0 was assigned, and b) a control which was assigned the value 10, corresponding to the softness result achieved with the product QUARTAMIN[7] D86P marketed by KAO Corporation, S.A., which is hydrogenated tallow dialkyldimethylammonium chloride, a conventional quaternary softening compound recognized as highly effective, although with poorer ecological tolerance owing to the fact that it has no ester groups intercalated in its hydrophobic chains. The results obtained are shown in Table 3.

TABLE 3

Softness tests on fabrics

| Active softening substance | Softness |
|---|---|
| Alkanolamine ester salt of Example 17 | 8 |
| Esterquat of Example 18 | 9 |
| Esterquat of Example 19 | 8 |
| Esterquat of Example 21 | 9 |
| Esterquat of Example 29 | 8 |
| Esterquat of Example 30 | 9 |
| Esterquat of Example 32 | 8 |
| QUARTAMIN[7] D86P (comparative control) | 10 |
| TETRANYL[7] AT-7590 | 7 |

TETRANYL[7] AT-7590 is a conventional esterquat derived from triethanolamine, marketed by KAO Corporation, S. A.

It can clearly be inferred from the results set out in Table 3 that the active softening substances composed of the cationic surfactants of the invention provide a softening efficacy superior to that of conventional esterquats and, in some cases, close to that achieved with the control product which is generally recognized for its high degree of softening efficacy.

Examples 34 to 50

Aqueous Fabric-softening Compositions

The softening compositions set out in Table 4, in which the percentages indicated are relative to the total weight of the composition, were prepared by conventional stirring and mixing methods. The softening efficacy of the compositions was evaluated by the method described in Example 31.

TABLE 4

Aqueous fabric-softening compositions and their softening efficacy.

| Ex. | Active softening substance[A] | Non-ionic surfactant | $Cl_2Mg$ | Minority constituents[B] and water | Softness |
|---|---|---|---|---|---|
| 34 | Esterquat Example 18 (2.5%) TETRANYL[7] AT-7590 (2.5%) | — | — | to 100% | 9 |
| 35 | Esterquat Example 19 (2%) TETRANYL[7] AT-7590 (14%) | LEVENOL[7] C-421 (4%) | 0.1% | to 100% | 10 |
| 36 | Esterquat example 20 (4%) TETRANYL[7] L1/90 (2.5%) | — | — | to 100% | 10 |
| 37 | Esterquat Example 21 (0.5%) KAOSOFT[7] PH (4.5%) | — | — | to 100% | 11 |
| 38 | Esterquat Example 22 (20%) | — | — | to 100% | 9 |
| 39 | Cationic salt Example 17 (2%) KAOSOFT[7] 1 (14%) | KAOPAN[7] SP-120 (3%) | 0.15% | to 100% | 11 |
| 40 | Esterquat example 23 (0.5%) TETRANYL[7] AT-7590 (4.5%) | — | — | to 100% | 10 |
| 41 | Esterquat Example 24 (0.25%) TETRANYL[7] AT-7590 (4.75%) | Pentaerythritol tetrastearate (1%) | 0.2% | to 100% | 8 |
| 42 | Esterquat Example 25 (1%) TETRANYL[7] AT-7590 (4%) | — | — | to 100% | 8 |
| 43 | Esterquat Example 26 (2.5%) TETRANYL[7] PH-5 (2.5%) | — | — | to 100% | 9 |
| 44 | Esterquat Example 20 (1%) QUARTAMIN[7] D86P (4%) | — | — | to 100% | 11 |
| 45 | Esterquat Example 27 (5%) | Glycerol monostearate (1%) | — | to 100% | 9 |
| 46 | Esterquat Example 29 (0.5%) TETRANYL[7] AT-7590 (4.5%) | — | — | to 100% | 9 |
| 47 | Esterquat Example 30 (0.25%) TETRANYL[7] AT-7590 (4.75%) | — | — | to 100% | 8 |
| 48 | Esterquat Example 31 (19.6%) | — | — | to 100% | 8 |
| 49 | Esterquat Example 31 (15%) | — | — | to 100% | 8 |

TABLE 4-continued

Aqueous fabric-softening compositions and their softening efficacy.

| Ex. | Active softening substance[A] | Non-ionic surfactant | Cl$_2$Mg | Minority constituents[B] and water | Softness |
|---|---|---|---|---|---|
| 50 | Esterquat Example 32 (1%) TETRANYL[7] AT-7590 (4%) | — | — | to 100% | 8 |

[A]Dry active substance relative to the total weight of the composition
[B]Perfumes, colouring substances, preservatives, etc.
In Table 4:
TETRANYL[7] AT-7590 is a conventional esterquat derived from triethanolamine, marketed by KAO Corporation, S.A.
TETRANYL[7] L1-90 is a conventional esterquat derived from triethanolamine, marketed by KAO Corporation, S.A.
KAOSOFT[7] PH is a conventional esterquat derived from methyl diethanolamine, marketed by KAO Corporation, S.A.
KAOSOFT[7] 1 is an amidoester marketed by KAO Corporation.
TETRANYL[7] PH-5 is a cationic oligomeric product marketed by KAO Corporation, S.A.
QUARTAMIN[7] D86P is a hydrogenated tallow dialkyl dimethylammonium chloride marketed by KAO Corporation, S.A.
LEVENOL[7] C-421 is an ethoxylated glycerol ester marketed by KAO Corporation, S.A.
KAOPAN[7] SP-120 is a sorbitan ester marketed by KAO Corporation, S.A.

The softness results set out in Table 4 show that all of the compositions exhibited a high degree of softening efficacy, and it is to be emphasized that the use of the cationic surfactants of the invention as additives, mixed with other active softening substances considerably improves their softening efficacy, particularly in the case of conventional esterquats derived from triethanolamine and methyl diethanolamine.

Modifications which do not affect, alter, change or modify the essential aspects of the esters described are included within the scope of the present invention.

Softener compositions described in examples 48 and 49, exhibit a good softening performance as well as a clear appearance without the use of any solvent.

What is claimed is:

1. Alkanolamine esters obtainable by the esterification reaction of an alkanolamine of general formula (I)

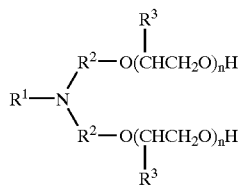  (I)

with a dicarboxylic acid or with a reactive derivative thereof, of general formula (II)

HOOC—R$^4$—COOH   (II)

and with a fatty alcohol, optionally alkoxylated, of general formula (III)

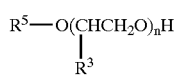  (III)

in which R$^1$ is hydrogen, a C$_1$–C$_6$ alkyl group, or the residue

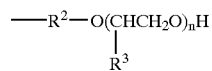

R$^2$ is a C$_1$–C$_6$ alkylene group, R$^3$ is hydrogen or methyl, n is 0 or a whole number between 1 and 20, R$^4$ is a C$_1$–C$_{36}$ alkylene group, optionally substituted or unsaturated, or an arylene group, and R$^5$ is a linear or branched C$_2$–C$_{22}$ alkyl or alkenyl group, wherein the molar ratio of the dicarboxylic acid to the alkanolamine is between 0.3 and 0.9.

2. Alkanolamine esters according to claim 1, characterized in that the alkanolamine of formula (I) is selected from triethanolamine, N-methyl diethanolamine, N-methyl diisopropanolamine, and triisopropanolamine, optionally alkoxylated with ethylene oxide or propylene oxide, or mixtures thereof.

3. Alkanolamine esters according to claim 1, characterized in that the dicarboxylic acid of formula (II) is selected from succinic, malic, glutaric, adipic, sebacic, pimelic, suberic, maleic, and terephthalic acids and those which are obtained by thermal oligomerization of unsaturated fatty acids, or mixtures thereof.

4. Alkanolamine esters according to claim 1, characterized in that the fatty alcohols of formula (III) are selected from those derived from fats and oils of natural origin, optionally hydrogenated and/or alkoxylated.

5. Alkanolamine esters according to claim 1, characterized in that the fatty alcohols of formula (III) are selected from hydrogenated or non-hydrogenated fatty alcohols derived from tallow, palm, olive, coconut, sunflower, soya, grape marc or rape, optionally alkoxylated with ethylene oxide or propylene oxide.

6. Alkanolamine esters according to claim 1, characterized in that, with regard to the reagents which take part in the esterification reaction: the molar ratio of the amount of the fatty alcohol to the alkanolamine is between 0.2 and 2.0.

7. Alkanolamine esters according to claim 6, characterized in that the molar ratio of the dicarboxylic acid to the alkanolamine is between 0.4 and 0.8.

8. Alkanolamine esters according to claim 1, characterized in that the esterification reaction is performed by condensation of the dicarboxylic acid with a mixture of the alkanolamine and the fatty alcohol, at a temperature of between 120° C. and 220° C. for a period of from 2 to 10 hours, and optionally at a reduced pressure of from 5 to 200 mbar and in the presence of an esterification catalyst.

9. Cationic surfactants obtainable by the formation of the addition salts of the alkanolamine esters of claim 1 with mineral or organic acids.

10. Cationic surfactants according to claim 9, characterized in that the mineral or organic acids are selected from hydrochloric, sulphuric, phosphoric, citric and lactic acids.

11. Esterquats obtainable by quaternization of the alkanolamine esters of claim 1 by the reaction with alkylation agents.

12. Esterquats according to claim 11, characterized in that the alkylation agents are selected from methyl chloride, methyl bromide, dimethyl sulphate, diethyl sulphate, and dimethyl carbonate.

13. A method of treating softening and/or conditioning treatment of natural or synthetic fiber, textile, paper fiber or hair fiber with the esterquats of the claim 11 or the cationic surfactant of the claim 9.

14. Aqueous fabric-softening compositions which comprise:
   (a) the surfactants or esterquats of claim 9 or 11,
   (b) one or a plurality of cationic surfactant active as fabric softeners,
   (c) one or a plurality of non-ionic fabric-conditioning surfactants, in which the total amount of components (a), (b) and (c) is between 2% and 60% by weight in a manner such that, with respect to the total amount of the said components (a), (b) and (c),
      (i) the proportion by weight of component (a) is between 2% and 99%,
      (ii) the proportion by weight of component (b) is between 0% and 98%,
      (v) the proportion by weight of component (c) is between 0% and 40%, and
      (vi) the proportion by weight of the total amount of (b) and (c) is between 1% and 98%.

15. Compositions according to claim 14, characterized in that the total amount of components (a), (b) and (c) is between 3% and 40% by weight,
   (i) the proportion by weight of component (a) is between 3% and 80%,
   (ii) the proportion by weight of component (b) is between 0% and 97%,
   (v) the proportion by weight of component (c) is between 0% and 30%, and
   (vi) the proportion by weight of the total amount of (b) and (c) is between 20% and 97%.

* * * * *

UNITED STATES PATENT AND TRADEMARK OFFICE
CERTIFICATE OF CORRECTION

PATENT NO.    : 6,465,419 B1
DATED         : October 15, 2002
INVENTOR(S)   : Bermejo et al.

It is certified that error appears in the above-identified patent and that said Letters Patent is hereby corrected as shown below:

<u>Title page,</u>
Item [12], should read:

-- [12] United States Patent
      Bermejo et al. --
Item [75], should read:

-- [75]  Inventors:  Maria José Osés Bermejo; Josep Ferrer Vilaret; Marisa Tomás Mumbrú, all of Barcelona (ES) --

Signed and Sealed this

Twentieth Day of April, 2004

JON W. DUDAS
*Acting Director of the United States Patent and Trademark Office*